(12) United States Patent
Eggenberger et al.

(10) Patent No.: US 9,179,847 B2
(45) Date of Patent: Nov. 10, 2015

(54) SYSTEM AND METHOD TO PROVIDE CAREER COUNSELING AND MANAGEMENT USING BIOFEEDBACK

(75) Inventors: Christian Eggenberger, Zurich (SZ); Peter Kenneth Malkin, Hawthorne, NY (US); Andreas Johannes Schindler, Zurich (SZ); Jeffrey William Mersereau, Bakersfield, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1431 days.

(21) Appl. No.: 12/504,238

(22) Filed: Jul. 16, 2009

(65) Prior Publication Data

US 2011/0015497 A1  Jan. 20, 2011

(51) Int. Cl.
  *A61B 5/00* (2006.01)
  *A61B 5/024* (2006.01)
  *A61B 5/16* (2006.01)
  *G06Q 30/02* (2012.01)

(52) U.S. Cl.
  CPC ............ *A61B 5/024* (2013.01); *A61B 5/02405* (2013.01); *A61B 5/165* (2013.01); *A61B 5/167* (2013.01); *G06Q 30/02* (2013.01)

(58) Field of Classification Search
  USPC .................. 600/300–301; 434/236
  See application file for complete search history.

(56) References Cited

U.S. PATENT DOCUMENTS

| | | | |
|---|---|---|---|
| 6,435,878 B1* | 8/2002 | Reynolds et al. | 434/236 |
| 2002/0019586 A1* | 2/2002 | Teller et al. | 600/300 |
| 2002/0106617 A1* | 8/2002 | Hersh | 434/236 |
| 2002/0188178 A1* | 12/2002 | Toeppen-Sprigg | 600/300 |
| 2004/0122702 A1* | 6/2004 | Sabol et al. | 705/2 |
| 2004/0147817 A1* | 7/2004 | Dewing et al. | 600/300 |
| 2004/0230105 A1* | 11/2004 | Geva et al. | 600/301 |
| 2005/0250081 A1* | 11/2005 | Salladay | 434/236 |
| 2007/0100246 A1* | 5/2007 | Hyde | 600/509 |
| 2007/0105080 A1* | 5/2007 | Hersh | 434/236 |
| 2007/0224580 A1* | 9/2007 | McFaul | 434/236 |
| 2007/0254270 A1* | 11/2007 | Hersh | 434/236 |
| 2008/0227063 A1* | 9/2008 | Kenedy et al. | 434/219 |
| 2008/0228043 A1* | 9/2008 | Kenedy et al. | 600/300 |
| 2009/0182578 A1* | 7/2009 | Ozersky | 705/3 |
| 2009/0216137 A1* | 8/2009 | Holland | 600/508 |
| 2009/0292180 A1* | 11/2009 | Mirow | 600/301 |
| 2010/0076333 A9* | 3/2010 | Burton et al. | 600/544 |
| 2010/0292545 A1* | 11/2010 | Berka et al. | 600/301 |
| 2014/0276243 A1* | 9/2014 | Van Dantzig et al. | 600/595 |

OTHER PUBLICATIONS

Maximilian Moser et al., The Symphony of Life, IEEE Engineering in Medicine and Biology Magazine, Jan./Feb. 2008, 9 pages.
Autonam Talent, Autonom Talent Consulting GmbH, http://autonomtalent.com, Website, May 2007, 1 page.

* cited by examiner

*Primary Examiner* — William Thomson
*Assistant Examiner* — Bobby Soriano
(74) *Attorney, Agent, or Firm* — Tutunjian & Bitetto, P.C.; Louis J. Percello

(57) ABSTRACT

An apparatus and method for measuring a person's biometric data as well as associated data and for using that data to determine the person's talents and well-being state, as well as predicting an optimal career path for the person. Biometric data is measured using a sensor, a memory configured to store the biometric signals, a database configured to store and retrieve profiles, and a processor configured to compare biometric data as well as associated data with anonymous profiles stored in the database and create a profile for the person.

22 Claims, 8 Drawing Sheets

SYSTEM AND METHOD TO PROVIDE CAREER COUNSELING AND MANAGEMENT USING BIOFEEDBACK

BACKGROUND

1. Technical Field

The present invention relates to biofeedback methods and devices, and more particularly to systems and methods for career consulting and management using biometric information such as heart rate variability data.

2. Description of the Related Art

Currently, career-based consulting and management is based on either a given employee's performance ratings (e.g., measured by client satisfaction surveys, 360° peer or manager surveys), or on the results of questionnaires or interviews answered by the given employee. Both of these fundamental source types have their limitations. Job performance results can be highly influenced by elements such as interpersonal relationships between the given employee and others, e.g., their manager, or job location. Answers to questionnaires or interviews are limited in that the given answers are in one extreme either wholly true (perhaps due to a given employee's modesty), or at the other extreme greatly exaggerated (if the interviewee is trying to inflate his or her capabilities and/or accomplishments). The process of interviewing employees can also be costly and time consuming, and bears the risk that only part of all potential talents are discovered and monitored.

SUMMARY

A system for creating biometric profiles includes a sensor configured to measure a person's biometric signals. A memory is configured to store the measured biometric signals. A database stores and retrieves biometric profiles. A processor compares biometric data stored in the memory to biometric profiles stored in the database and creates a biometric profile for the person.

A method for determining an optimal job for a given user includes measuring biometric data of a given user. The biometric data is then used to determine characteristic traits of the given user. The user is then matched to a job role based upon the determined characteristic traits.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

Detailed Description Of Preferred Embodiments

Figure 1:
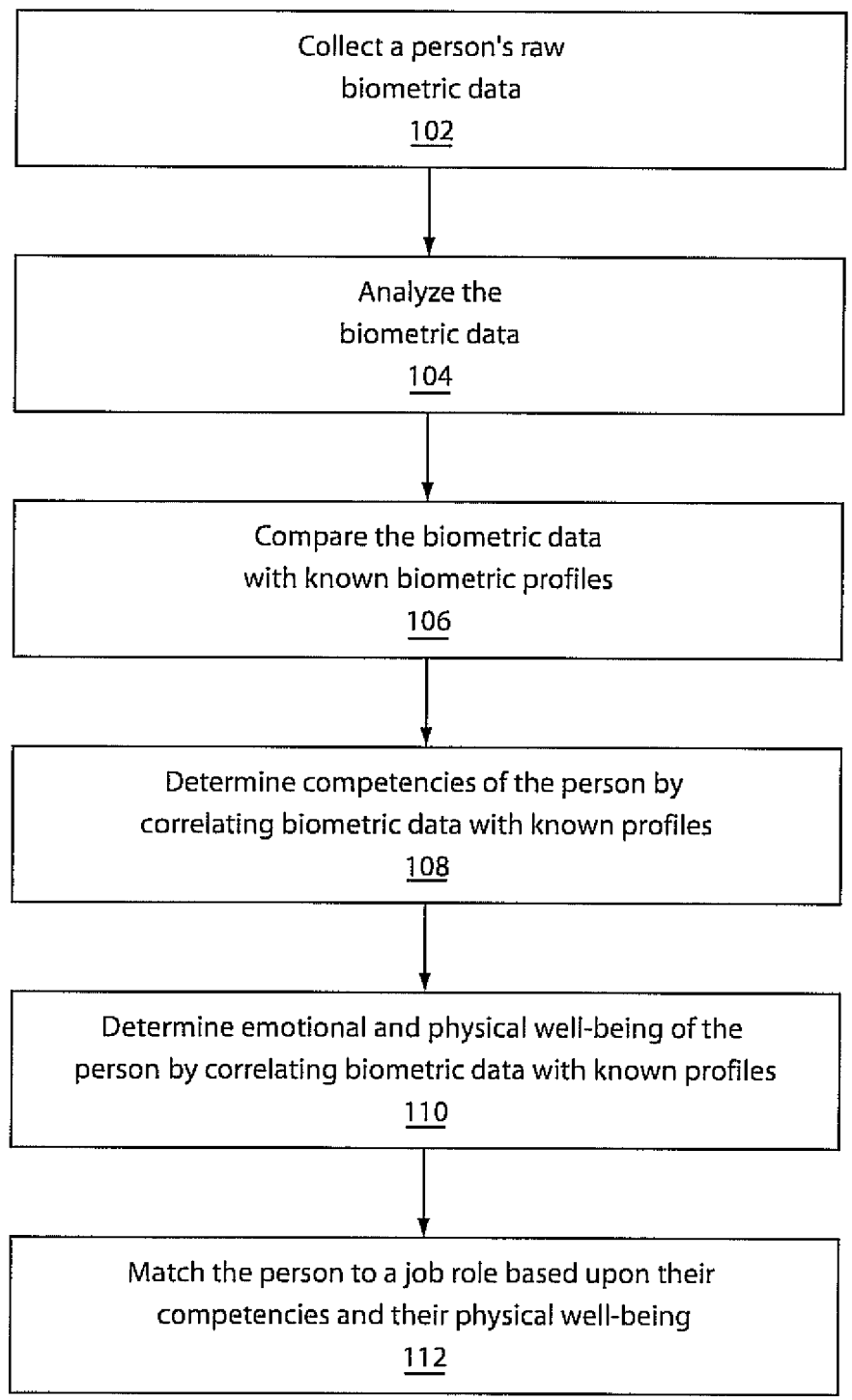
FIG. 1 is a block diagram of a method for matching a person to a job role based upon their competencies in accordance with an illustrative embodiment.

A person's bio-feedback is a good indicator of who a person is and how that person is feeling. Bio-feedback can indicate not only the person's physical well-being, but also their emotional well-being state and their talents. The present principles are directed to a system and method which measures a person's biometric data and builds a profile for that person representing the person's talents and well-being state. The profile may also include associated data, such as the person's competencies and traits. It compares the measured profile to other profiles corresponding to a plurality of previously measured people, and provides indications as to what sort of roles the person would be best suited to.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software packager partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Certain biometric signals have been shown to be an indicator not only of the person's physical well-being, but also an indicator of the person's emotional well-being, as well as more abstract personality traits, such as, e.g., capacity for achievement, innovation, and intuition. The way a person's biometric signals change over a period of time provides an indication as to the condition and potential of that person. After measuring the person's biometric data over the course of a period of time and analyzing the data with mathematical transform suited to the type of signal, the resulting data can be compared to a database of other people's previously accumulated biometric data profiles to determine the person's attributes. These accumulated profiles have associated with them the known traits, competencies, and well-being states of their respective users.

The information gleaned from the biometric data analysis can then be used to counsel the person with regard to, for example, career path and well-being activities.

Referring now in detail to the figures in which like numerals represent the same or similar elements and initially to FIG. 1, an exemplary method for matching a person to a job role based on their competencies is illustratively depicted. In block 102, raw biometric data is collected for the person over a period of time. It is contemplated that this data can include any of a number of different forms of biometric data (e.g., skin conductivity, brainwaves, blood sugar levels, or other signals from the sympathetic or parasympathetic nervous systems) but for the sake of simplicity only heart rate variability is described herein.

At block 104, the raw biometric data is processed to form a biometric profile. Block 106 compares the biometric profile to a database of known biometric profiles. Block 108 uses correlations between the measured biometric profile and the stored biometric profiles to determine the competencies of the person. Block 110 uses correlations between the measured biometric profile and the stored biometric profiles to determine the person's physical well-being. A person's internal state, their health, and their talents are made manifest by their body's reactions. For example, the body reacts naturally to stress, and it produces different responses depending on a person's ability to handle stressful situations. By measuring the person's autonomic responses, it is possible to gain significant insight into that person.

Taking the person's competencies and well-being into account, block 112 matches the person to the best available job role. As an example, using this method, one could detect that the person is highly negatively stressed and give him/her a relaxing job role or a positive stress producing job role which will give him/her an opportunity to recover. If a person is exceptionally talented, he/she may receive job roles which allow him/her make best use of his or her talents. This makes it possible to help the person reach his or her potential while staying healthy and productive. It is contemplated that these traits and others might be accounted for in a person's profile.

Figure 2:
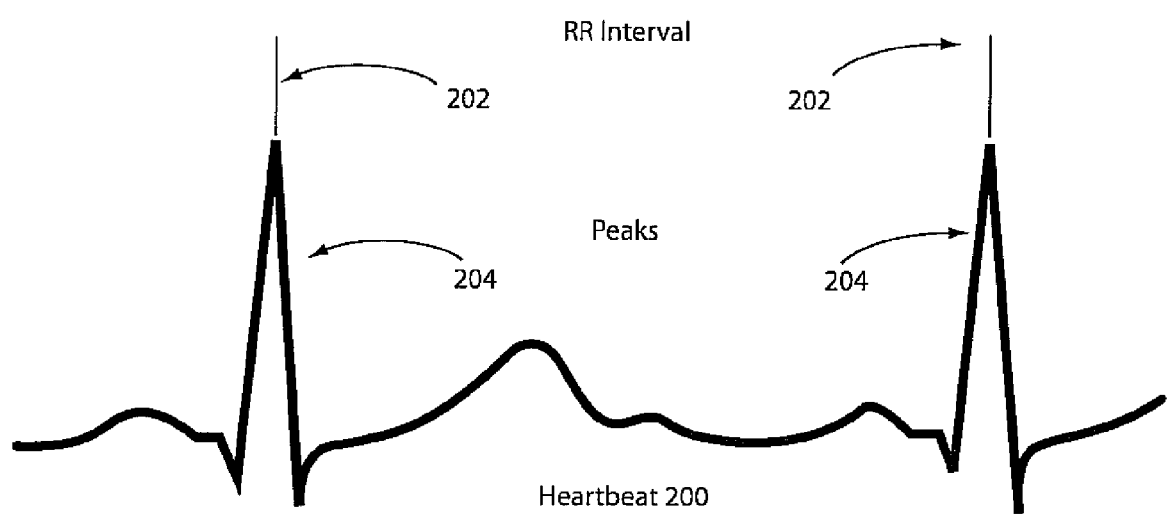
FIG. 2 is a graph depicting an example of a recorded heartbeat.

One example of biometric data that can be used for this purpose is Heart Rate Variability ("HRV"). HRV is a measurement of how the timing between heartbeats changes over time. A heartbeat graph 200 is illustratively shown in FIG. 2. The time between individual beats 204 is called the RR interval 202. "RR interval" is defined as the time between two "R waves" of an ECG. HRV is calculated by collecting data on the heartbeat 200 for a period of time (for example, 24 hours, although other periods are contemplated) and measuring each RR interval with a high sampling resolution (for example, 4,000 to 5,000 Hz). Calculating the standard deviation of the RR intervals over a given period of time yields a measurement of HRV: a low standard deviation indicates a low HRV, while a high standard deviation indicates a high HRV.

By performing a Fourier transform (or other mathematical transform) on the collected heartbeat data, one can produce a graph called a "life fire." FIGS. 3a-e are examples of different life fires. The horizontal axis represents time, while the vertical axis represents the frequencies at which the RR interval 102 is changing at that point in time. Darker colors represent larger amounts of change at those frequencies.

Figure 3A:
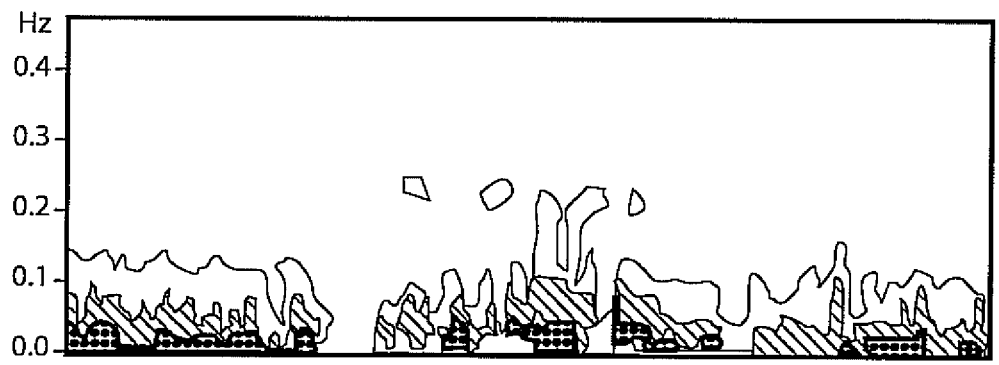
FIG. 3a is a graph plotting time versus frequency as an example of heart rate variability data characterizing achievement.
Figure 3B:
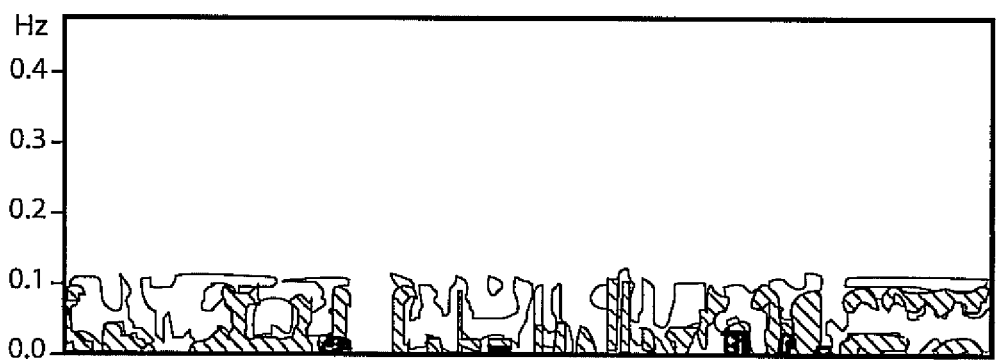
FIG. 3b is a graph plotting time versus frequency as an example of heart rate variability data characterizing will.
Figure 3C:
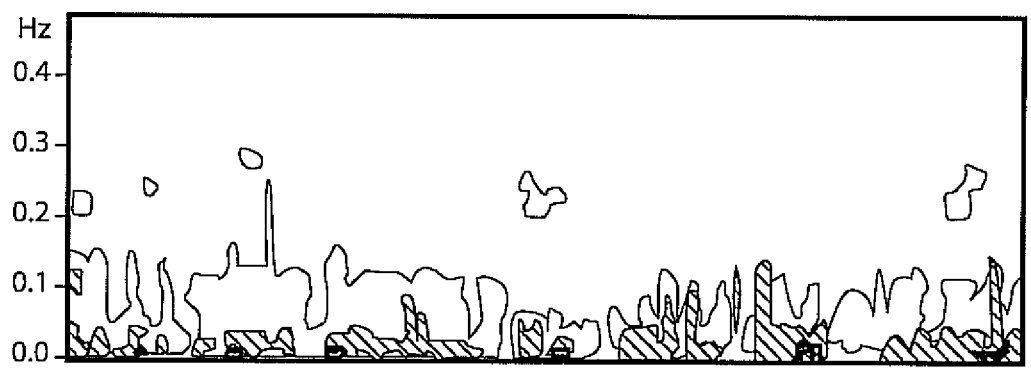
FIG. 3c is a graph plotting time versus frequency as an example of heart rate variability data characterizing intuition.
Figure 3D:
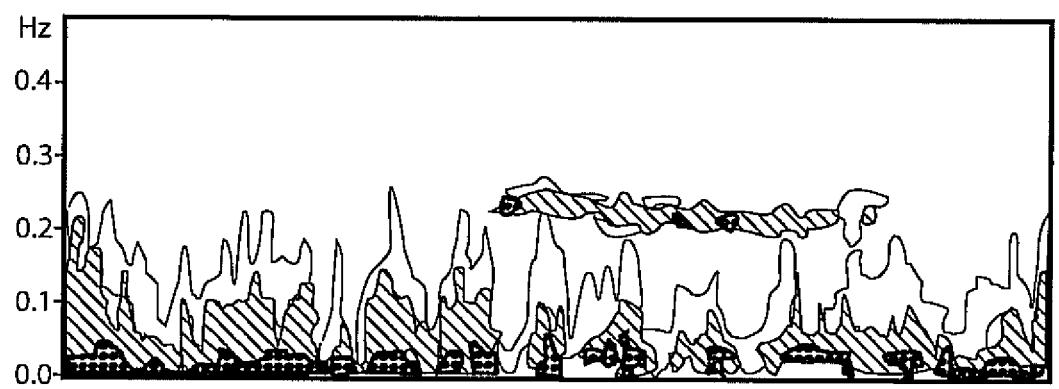
FIG. 3d is a graph plotting time versus frequency as an example of heart rate variability data characterizing change.
Figure 3E:
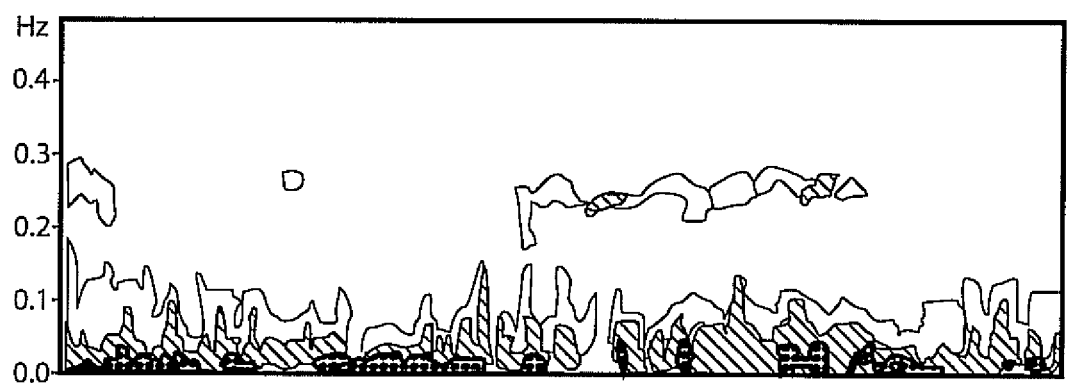
FIG. 3e is a graph plotting time versus frequency as an example of heart rate variability data characterizing innovation.

HRV information can then be correlated with the person's well-being state, as it is indicative of stress and sickness. HRV measurements can also be correlated with various personal traits. FIGS. 3a-e represent HRV measurements that, according to one model for interpretation, characterize people with high achievement (FIG. 3a), will (FIG. 3b), intuition (FIG. 3c), change (FIG. 3d), and innovation (FIG. 3e). In each of the figures, the dotted areas with thick lines represent frequencies which manifest the strongest, the areas with angled lines show medium frequencies, and the solid white areas are frequencies which manifest weakly. For example, according to this exemplary model, measuring a strong HRV response in the range 0.15 Hz to 0.4 Hz is an indication of having the talent "intuition," while a strong HRV response in the range 0.0033 Hz to 0.04 Hz is indicative of "achievement." Other ranges and combinations of ranges characterize other talents. These talents are intended to be purely exemplary, as another model may interpret the data as characterizing different traits, while still embodying the present principles. The result of using such a model is that concrete determinations may be made automatically by measuring HRV.

Figure 4:
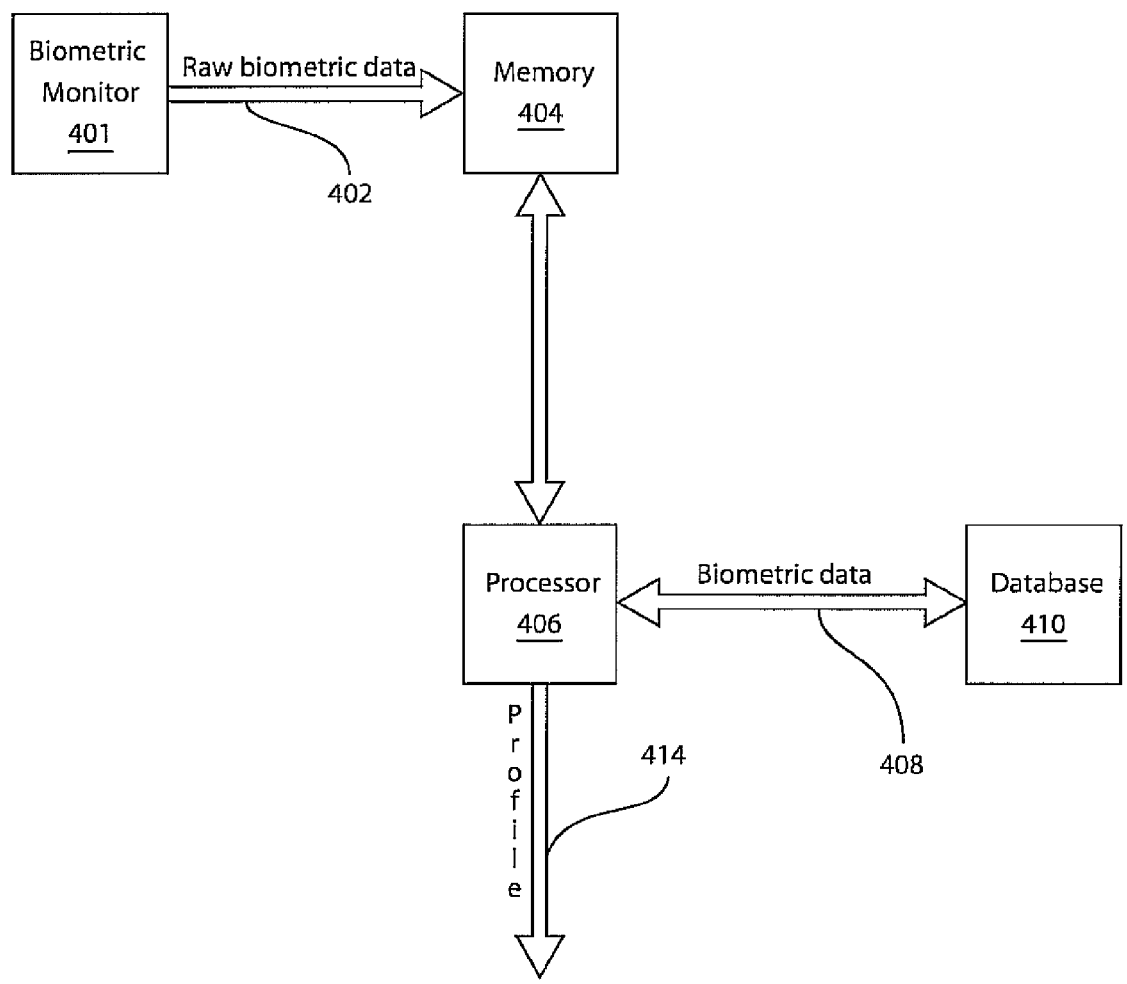
FIG. 4 is a block/flow diagram illustrating a system which generates a heart rate variability profile in accordance with an illustrative embodiment.

Referring to FIG. 4, an embodiment of a system/method 400 designed to measure a person's biometric data and correlate that data with the person's personal traits is illustratively shown. A biometric monitor 401, in one embodiment, for example, a heart rate monitor, tracks the person's biometric signals over a period of time. The raw biometric data 402 is then stored in a memory 404. After the data has been collected, a processor 406 analyzes the biometric data stored in memory 404. In the case of HRV, this means performing a transform of the data, e.g. a Fourier transform. The processor 406 then compares the analyzed biometric data 408 to biometric profiles 412 stored in a database 410. These biometric profiles 412 correspond to various known character and physical and emotional traits. The processor 406 builds a profile 414 for the biometric data 408 which describes the character and physical and emotional traits most likely possessed by the person.

Figure 5:
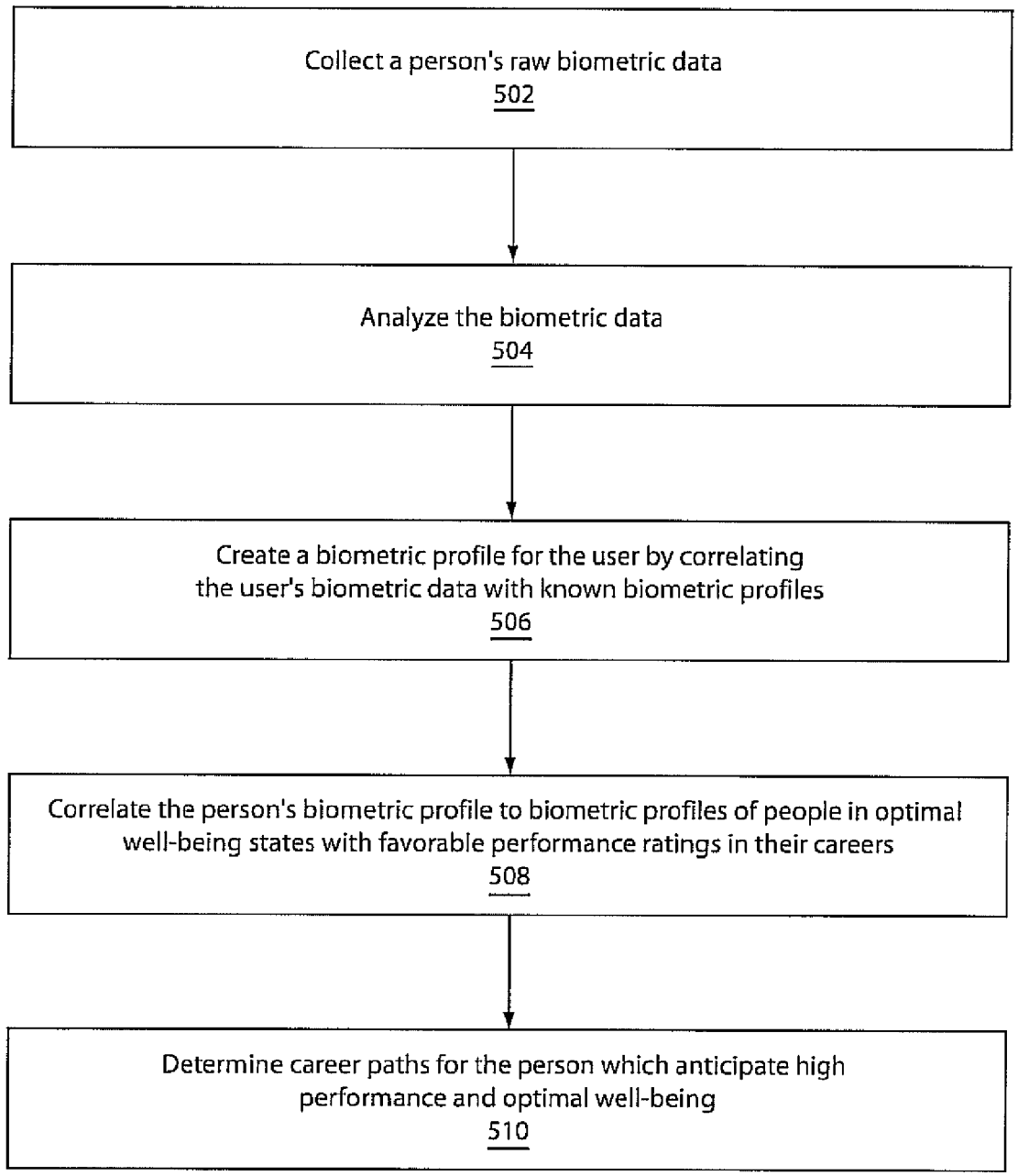
FIG. 5 is a block diagram of a method for determining a career path in which a person will perform well and maintain an optimal well-being in accordance with an illustrative embodiment.

The system just described can be used to perform the methods in accordance with the present principles. Referring to FIG. 5, a method for determining the optimal career path for a person is illustratively shown. Blocks 502 and 504 collect and analyze the raw biometric data, as in FIG. 1. Block 506 compares the biometric data with known biometric profiles. Block 508 matches the biometric data to people who have performed well in their careers, and block 510 suggests a career path for the person that will optimize their performance and well-being. For example, if a person has a profile similar to the profiles of successful managers and leaders, block 510 might involve determining that the person would be best suited for a career path that will lead to management. As another example, if a person's profile shows a high degree of adaptability, block 510 might involve determining that the person would be best suited for a high-paced role with quickly-changing conditions.

Figure 6:
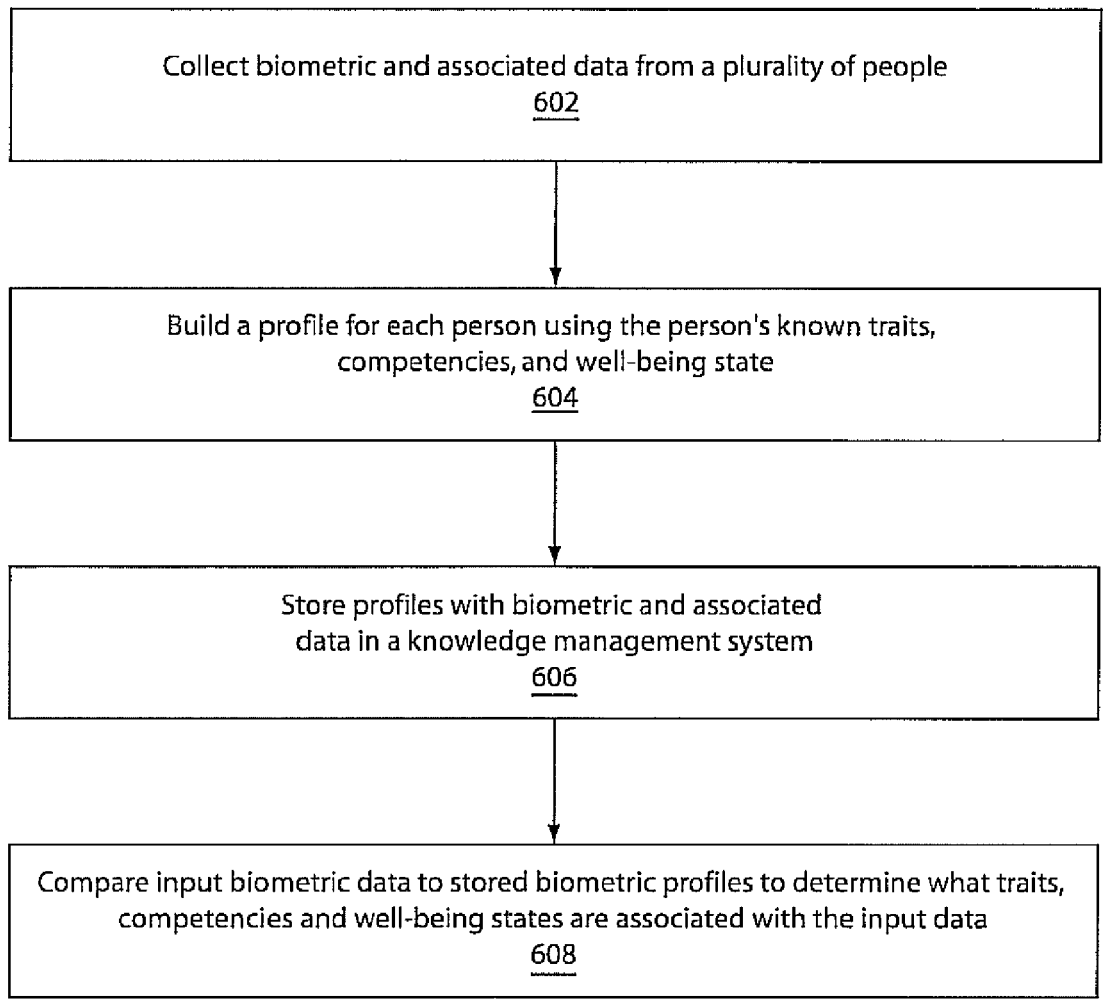
FIG. 6 is a block diagram of the steps required to build a set of biometric profiles.

Referring to FIG. 6, preliminary steps needed to make use of the methods of the present system/method are illustratively shown. Block 602 collects biometric data for a plurality of people. Block 604 then builds biometric profiles for the people "by hand," using a person's known traits, competencies, and well-beings states. Block 606 stores the profiles in a "knowledge management system." Once the biometric data and the associated data have been collected and the profiles have been created, the profiles should have no connection to the identity of the people they represent to protect the privacy of the people who make up the stored profiles. Once a plurality of profiles have been stored, block 608 uses the present principles to build new profiles from input biometric data, using correlations between the input data and the stored profiles.

Figure 7:
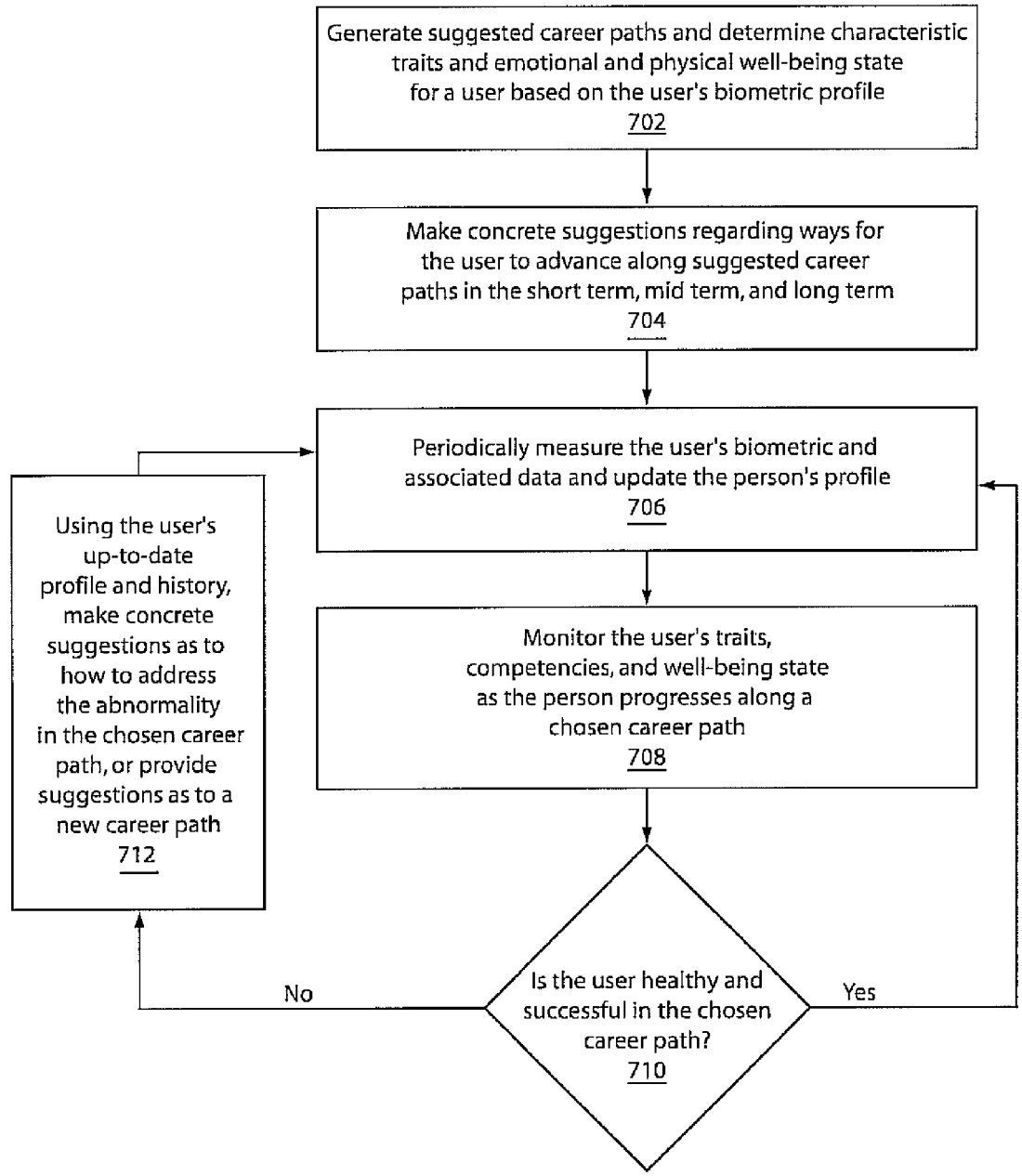
FIG. 7 is a block diagram of a method for providing ongoing career counseling to a user.

Referring to FIG. 7, a method for providing responsive guidance to a user is illustratively shown. Block 702 generates suggested career paths, competencies, and a well-being state for the user as shown, for example, in FIG. 5. In block 704, an advisor can then make a recommendation to the person regarding appropriate tasks, open positions, well-being and learning activities, and what measures he or she has to make short-term, mid-term, and long-term advancements on the suggested career paths. These recommendations are geared to be advisory, so that the person can make his or her own choices regarding his or her career path. Although the advisor may be a human, it is also contemplated that an automated system may fill that role.

For example, consider a person applying for a job. The person is just now entering the workforce and has little idea of what roles or career paths he or she would be best suited for. The person is provided with a biometric sensor which monitors their biometric data for several hours. During this time the person performs a standardized set of activities or keeps a logbook of activities performed. The sensor stores the biometric information using a memory device, or transmits the data to a database or computer. The data is retrieved and analyzed using one or more of the techniques listed above. Conclusions are drawn based upon the comparisons as to whether the person is well-suited for the job. This provides benefits to the person, because he or she will not end up in a job that is significantly above or below his or her ability, and it provides benefits to the employer, because the employer can streamline the hiring process.

Another example is a person who has been in the workforce for some time, but who, due to changed circumstances or the simple passage of time, has realized that he or she is no longer interested or well-suited to his or her job role. The person may then speak to a career counselor who makes use of the present system and methods to make recommendations. This can lead the person to pursue a new career path that he or she will be more successful at, and will find more fulfilling.

In block 706, the person may continue to obtain periodic measurements of their biometric data as well as the associated data. Block 708 shows that these subsequent measurements will allow the advisor to build a history and track the person's advancement along the proposed career path. Such monitoring also makes it possible to note any abnormalities with regard to the person's job performance and health (i.e., when the person is neither successful in his or her job role, nor healthy). If an abnormality is detected in block 710, the advisor makes suggestions regarding changes that the person can make to get back on track, or suggestions regarding a new career path that will better suit the user's current characteristic traits and well-being state.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope and spirit of the invention as outlined by the appended claims. Having thus described aspects of the invention, with the details and particularity required by the patent laws, what is claimed and desired protected by Letters Patent is set forth in the appended claims.

What is claimed is:

1. A system for creating biometric profiles comprising:
    a sensor configured to measure a person's biometric signals;
    memory configured to store the biometric signals;
    a database configured to store and retrieve biometric profiles; and
    a processor configured to process the biometric signals to produce a life fire graph, comprising a heat map that correlates an intensity of change in the biometric signals at different frequencies at different points in time, configured to compare the life fire graph to a plurality of biometric profiles stored in the database, and configured to evaluate at least one personality characteristic of the person based on correlations with the plurality of stored profiles.

2. The system of claim 1, wherein the measured biometric data includes Heart Rate Variability data.

3. The system of claim 1, wherein the measured biometric data includes skin conductivity.

4. The system of claim 1, wherein the measured biometric data includes brainwaves.

5. The system of claim 1, wherein the database includes a knowledge management system where at least one of competency, associated well-being state, and an associated performance rating of a plurality of users are stored.

6. The system of claim 1, wherein the processor includes an alert mechanism which is triggered when a mismatch occurs between a given person's biometric data and a job role.

7. The system of claim 1, wherein the sensor, memory, database, and processor are contained within a single, self-contained device that is small enough to be worn under a user's clothing.

8. A method for determining an optimal job for a given user comprising:
    creating a biometric profile for a given user, including the user's physical and mental characteristic traits, by processing biometric signals to produce a life fire graph, comprising a heat map that correlates an intensity of change in the biometric signals at different frequencies at different points in time;
    correlating the user's biometric profile with a plurality of known biometric profiles using a processor to determine job roles with a high probability of good performance and health for the user; and
    matching the given user to a job role based upon the characteristic traits of the given user's biometric profile.

9. The method of claim 8, wherein the biometric data includes Heart Rate Variability information.

10. The method of claim 8, wherein the characteristic traits include at least one competency.

11. The method of claim 8, wherein the characteristic traits include the given user's well-being state.

12. The method of claim 11, wherein the information to determine the characteristic traits and the matching job role are retrieved from a knowledge management system where the characteristic traits and the associated performance rating of a significant number of users are stored.

13. The method of claim 12 wherein a competency includes information about personal characteristics such as motives, traits, self-image, social role, and information about the skills and knowledge of a user.

14. A computer program medium comprising a computer useable storage medium including a computer readable program, wherein the computer readable program when executed on a computer causes the computer to perform the method of claim 8.

15. A method for determining a career path for a given user comprising:
    creating a biometric profile for a given user, by processing biometric signals to produce a life fire graph, comprising a heat map that correlates an intensity of change in the biometric signals at different frequencies at different points in time;
    matching the biometric profile of the given user with current and historical biometric profiles of users in an optimal well-being state with favorable performance ratings in a career using a processor; and
    generating potential career paths for the given user which anticipate favorable performance ratings and an optimal well-being state.

16. The method of claim 15, wherein the measured biometric data includes Heart Rate Variability.

17. The method of claim 15, further comprising making recommendations by an advisor to the given user regarding measures the user has to take in order to make short-term, mid-term, and long-term advancements on the generated career paths.

18. The method of claim 17, wherein the recommendation regards tasks, open positions, well-being activities and learning activities which are appropriate for the progression of the given user along the potential career paths.

19. The method of claim 15, wherein the performance and well-being state of the person is periodically monitored with respect to a chosen career path.

20. The method of claim 19, wherein the system generates a list of solutions as soon the performance information and well-being information indicate an abnormality from the chosen career path.

21. A computer program medium comprising a computer useable storage medium including a computer readable program, wherein the computer readable program when executed on a computer causes the computer to perform the method of claim 15.

22. The system of claim 1, wherein the processor is further configured to process the biometric signals using a Fourier transform.

* * * * *